(12) United States Patent
Farrell et al.

(10) Patent No.: US 6,310,047 B1
(45) Date of Patent: Oct. 30, 2001

(54) HIGH AFFINITY DNA BINDING COMPOUNDS AS ADJUVANTS IN ANTISENSE TECHNOLOGY

(75) Inventors: Nicholas Farrell; Miriam Kloster, both of Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/379,718

(22) Filed: Aug. 24, 1999

(51) Int. Cl.[7] .......................... C07F 15/00; A61K 31/28; A61K 31/70; C12Q 1/68; C12N 5/00
(52) U.S. Cl. ..................... 514/44; 556/136; 556/137; 435/6; 435/325; 435/375; 514/492; 536/23.1
(58) Field of Search ...................................... 556/137, 136; 514/492, 44, 187; 536/23.1; 435/6, 325, 375

(56) References Cited

PUBLICATIONS

Johnson et al. Nucleic Acids Research, vol. 20, No. 7, pp. 1697–1703, 1992.*
Wu et al. Journal of Inorganic Biochemistry. vol. 63, pp. 9–18, 1996.*

\* cited by examiner

*Primary Examiner*—John L. LeGuyader
*Assistant Examiner*—Janet Epps
(74) *Attorney, Agent, or Firm*—McGuireWoods, LLP (57) ABSTRACT

The invention provides an improved method for the delivery and stabilization of antisense oligodeoxynucleotides (ODNs) to cells. The unmodified ODNs are complexed to a polynuclear platinum compound or to a structural derivative thereof. Complexation neutralizes the charge of the ODN and makes possible its passage into the cell, without the addition of other transfection agents. The invention may be used in the treatment any disease which is amenable to treatment by antisense ODNs. In addition, the invention provides a new method specifically for the treatment of cancer.

20 Claims, 5 Drawing Sheets

SEQUENCE LISTING

<160> NUMBER OF SEQ ID NOS: 5

<210> SEQ ID NO: 1
<211> LENGTH: 20
<212> TYPE: DNA
<213> ORGANISM: Artificial Sequence

```
<220> FEATURE:
<223> OTHER INFORMATION: Description of Artificial Sequence: synthetic
      oligonucleotides for gene therapy

<400> SEQUENCE: 1
cagcgtgcgc catccttccc                                                    20

<210> SEQ ID NO: 2
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotides for gene therapy

<400> SEQUENCE: 2
gggaaggatg gcgcacgctg                                                    20

<210> SEQ ID NO: 3
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotides for gene therapy

<400> SEQUENCE: 3
gcccaagctg gcatccgtca                                                    20

<210> SEQ ID NO: 4
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotides for gene therapy

<400> SEQUENCE: 4
gttctcgctg gtgagtttca                                                    20

<210> SEQ ID NO: 5
<211> LENGTH: 20
<212> TYPE: DNA
<213> ORGANISM: Artificial Sequence
<220> FEATURE:
<223> OTHER INFORMATION: Description of Combined DNA/RNA Molecule:
      synthetic oligonucleotide used to treat CMV-retinitis in AIDS
      patients
<220> FEATURE:
<223> OTHER INFORMATION: Description of Artificial Sequence: synthetic
      oligonucleotides for gene therapy

<400> SEQUENCE: 5 ugggcttac cttgcgaaca                                                     20
```

HIGH AFFINITY DNA BINDING COMPOUNDS AS ADJUVANTS IN ANTISENSE TECHNOLOGY

This invention was made using funds from grants from the National Institutes of Health having grant number 1RO1-CA78754-01. The government may have certain rights in this invention.

BACKGROUND OF THE INVENTION

1. Field of the Invention

The invention generally relates to the enhancement of the delivery of and the in vivo nuclease resistance of antisense oligodeoxynucleotides (ODNs). In particular, the invention provides high affinity DNA binding platinum compounds which bind antisense oligodeoxynucleotides, facilitate their delivery into the cell, and augment their in vivo nuclease resistance. Additionally, the invention provides a novel method for treating cancer.

2. Background of the Invention

Antisense technology is a rapidly developing field, with many compounds being evaluated in preclinical and clinical trials as therapeutic agents in cancer, viral infections, genetic disorders and as tools for functional genomic studies. The basic goal of antisense technology is to inhibit protein expression by the binding of small molecules to single-stranded messenger RNA. Protein expression is inhibited either by physically blocking the translational machinery or by inducing RNase H-mediated RNA degradation.

An ODN is a short (about 7–25 nucleotides) sequence of single-stranded DNA which is complementary to the mRNA which is to be inhibited. Once introduced into the cell, the ODN can bind to the mRNA and prevent its translation. However, the ODN must 1) enter the cell in sufficient quantities and 2) remain stable until bound to the mRNA. (for reviews see Crooke, 1998; Branch, 1998; and Lavrovsky, 1997).

Some of the possible antisense molecules in development include synthetic oligonucleotides (typically modified in the phosphate backbone, the sugar moiety, and/or the nucleobase) (Schmajuk, 1999; Crooke, 1997; Monia, 1997; Flanagan, Wolf et al, 1999; Flanagan, Wagner et al, 1999), morpholino oligonucleotides (Summerton and Weller, 1997), chemically conjugated oligonucleotides (Spiller et al., 1998), peptide nucleic acids (Good and Nielsen, 1997; Nielsen, 1999), and plasmid-derived RNA (Weiss, 1999; Inouye et al., 1997). Also under development are antisense molecules which use alternate strategies for degrading the mRNA-ribozyme-mediated cleavage of the mRNA (Arndt and Rank, 1997; Rossi, 1997), trans-splicing ribozymes (Kohler, 1999), oligonucleotide-based external guide sequences (EGSs) which are substrates for Rnase P (Guerrier-Takada et al., 1995; Ma, 1998), and 2',5'-oligoadenylate-chimeric molecules which are substrates for RNase L (Cramer, 1999; Verheijen, 1999; Xiao et al., 1998).

The initial use of phosphodiester oligonucleotides revealed very poor penetration into the cell and a very short half-life in sera, on the order of 15–60 minutes (Crooke, 1992). The first generation of modified oligonucleotides were created by the incorporation of a phosphorothioate backbone. These modified oligonucleotides exhibited enhanced cellular stability of the oligonucleotide (the cellular lifetime increased to 24–48 hours) and were substrates for RNase H. However, DNA-RNA duplex stability was lowered, and toxic side effects were created as a result of metabolites and non-specific binding to proteins. Pharmacokinetic properties, tissue distribution, and in vivo stability data are now becoming available for these first generation antisense molecules. So far, the data indicate the need for improved modifications that will increase potency and decrease cytotoxicity (Agrawal, 1996; Juliano, 1999).

Chemistries that modify the sugar rather than the backbone of the oligonucleotide, such as 2'-O-methyl and 2'-O-methoxyethyl analogs (McKay et al., 1996; Monia, 1997; Monia et al., 1993) are the second generation of antisense oligonucleotides. These modifications increase DNA-RNA duplex stability, show partial resistance to nucleases, and have a lower toxicity than the corresponding phosphorothioate oligonucleotides. The major drawback of these modifications is the inhibition of the RNase H mechanism which is necessary for degrading the targeted mRNA; there is no antisense effect because the mRNA can be translated into functional protein. Currently, mixed-backbone oligonucleotides, chimeric oligomers that incorporate both phosphorothioates and 2'-modified sugars, have become the method of choice. These molecules comprise a mixture of chemistries that attempt to optimize stability, specificity, nuclease resistance, and are still substrates for RNase H (Agrawal and Zhang, 1997; Crooke, 1997).

While engineering newer and better antisense oligomers remains important, focus has shifted to optimizing delivery and cellular localization of these molecules. Antisense molecules can enter the cell by passive diffusion or by receptor-mediated endocytosis, although the mechanism of oligonucleotide release from the endosome is not well understood. However, neither mechanism is efficient, resulting in little or no antisense molecule actually getting to its target. For example, leukemia MOLT-3 cells incubated with an unmodified phosphodiester oligonucleotide showed no cellular uptake and a fully-modified phosphorothioate oligonucleotide showed only 0.3% of the initial concentration of oligonucleotide incorporated into cells (Thierry and Dritschilo, 1992). Typically, high concentrations ($\mu$M) of antisense oligonucleotides are used to increase the intracellular concentration, which potentially leads to increased cytotoxicity.

Cellular uptake of antisense oligonucleotides in vitro can be dramatically improved through the use of uptake mediators such as cationic lipids, which capitalize on the electrostatic interaction between the positively-charged compound and the negatively-charged ODN for delivering the molecule to the nucleus (Hope et al., 1998). Many commercial cationic lipids exist; however, they have a tendency to aggregate and can be toxic at high concentrations. In addition, the ratio of transfection agent to oligomer is highly empirical and needs to be optimized for every cell line. An alternate method for packaging the antisense oligomer for cellular uptake is liposome encapsulation. Typically, these formulations involve a combination of cationic polymers, such as phosphotidylcholine or phosphotidylethanolamine, and lipophilic molecules (Gokhale et al., 1997).

Other novel transfection agents currently under development which take advantage of electrostatic interactions between the compound and the ODN include a molecular umbrella, which assists the delivery of oligomers through the lipid bilayer (Janout et al., 1997), water-soluble cationic porphyrins (Benimetskaya, 1998; Takle et al., 1997), and Starburst polyamidoamine dendrimers (Helin, 1999; Bielinska et al., 1996). Also under development are antisense molecules that are chemically conjugated to delivery enhancers such as lipophilic conjugates (Rump et al., 1998; Spiller et al., 1998), and fusion peptides containing both hydrophobic and hydrophilic sequences (Chaloin et al., 1998).

While much research has been directed toward the discovery of new modes of delivery of antisense ODNs, so far none have succeeded in surmounting the challenges of combining both efficient delivery of the ODN to the cell, and resistance to endogenous nucleases after delivery. Thus, there remains a need for new, simple and innovative methods for enhancing cellular uptake of and increasing the in vivo stability of antisense molecules.

SUMMARY OF THE INVENTION

It is an object of this invention to provide a method for the delivery of antisense oligodeoxynucleotides to cells by complexing the ODN to a polynuclear platinum compound, and delivering the complex to the cell. Complexation of the ODN with the Pt compound neutralizes the negative charge of the phosphodiester backbone of the ODN, thus making it easier to cross cellular membranes. In addition, the Pt compound, when bound to the ODN, confers added stability and resistance to degradation by nucleases.

One advantage of this method is that it is not necessary to chemically modify the ODN in any way; sequences with classical phophodiester backbones may be used. Thus, the synthesis of the ODN to be used in the practice of the present invention is relatively inexpensive. However, chemically modified ODNs may be used in the practice of the present invention if desired.

The invention provides compositions of matter comprised of an ODN complexed or associated with a polynuclear Pt compound. The polynuclear Pt compounds may be divided into three categories: 1) linear polynuclear Pt compounds 2) branched polynuclear Pt compounds and 3) heteronuclear compounds containing Pt and at least one other metal. The mode of binding between the ODN and the Pt compound may be either covalent or non-covalent.

Abbreviations

For a convenient abbreviation of polynuclear (platinum) complexes we have adopted a system where the numbers refer to the number of chlorides (or anionic leaving groups) on each platinum atom (See N. Farrell, *Comments in Inorganic Chemistry,* 16 (6), 373–389 (1995). The numbering refers to the number of leaving groups (especially chloride) on each Pt center and the lettering refers to the geometry of the Pt—Cl bond with respect to the nitrogen of the bridging diamine. Once these two parameters are specified, the geometry of the overall complex is automatically fixed. Thus, following this system of nomenclature, [{trans-PtCl(NH$_3$)$_2$}$_2$H$_2$N(CH$_2$)$_n$NH$_2$]Cl$_2$ is 1,1/t,t etc.

Specifying the chain length is done by a further extension. Thus, [{trans-PtCl(NH$_3$)$_2$}$_2$H$_2$N(CH$_2$)$_4$NH$_2$]Cl$_2$ is specifically 1,1/t,t n=4. Where there are no chloride or leaving groups on the Pt centers the compound is abbreviated simply 0,0— as in the [{trans-Pt(NH$_3$)$_2$}$_3$H$_2$N(CH$_2$)$_n$NH$_2$]$^{4+}$ cation. Chain length and geometry may be specified as before. Trinuclear and polynuclear compounds are abbreviated in a similar manner. Thus 1,0,1/t,t,t n=6,6 contains one Cl on the terminal Pt atom, no Cl on the central Pt unit; the geometry is all trans and the chain length of both bridging diamines is 6.

DETAILED DESCRIPTION OF THE PREFERRED EMBODIMENTS OF THE INVENTION

The present invention provides methods for enhancing the delivery and nuclease resistance of antisense ODNs through complexation with high affinity DNA binding polynuclear Pt compounds.

The mode of attachment of the compounds of the present invention to ODNs may be either covalent or non-covalent, depending on the conditions of the reaction. With respect to covalent binding, the structure of polynuclear platinum-DNA complexes in general suggests that binding occurs in several steps. Initial rapid electrostatic interactions based on charge (DNA is negatively charged, Pt compounds are positively charged) cause the molecules to form a complex. Electrostatic complexation may be followed by covalent attachment via relatively slow hydrolysis of a Pt-leaving group (e.g.Pt—Cl) bond which produces a Pt—H$_2$O species. The aquo (H$_2$O) ligand is then rapidly displaced by a suitable nucleobase such as, in the case of DNA, guanine.

Non-covalent attachment of the compounds of the present invention may be effected in two different ways. First, saline solution is known to prevent leaving group (e.g. chloride) hydrolysis, slowing the covalent binding reaction to DNA. Suitable concentrations of chloride ion may thus be used to control the rate of covalent binding (Wu, et al, 1996), and very high concentrations may be used to prevent covalent attachment altogether, resulting in a complex which remains non-covalently bound.

Secondly, in a further embodiment of the present invention, the compounds of the present invention may be chemically modified so that they associate with DNA only via non-covalent modes regardless of chloride concentrations. In this case, the compounds are chemically modified by displacement of a leaving group (e.g. Cl) by a non-leaving group (e.g. NH$_3$). Complexes formed between such chemically modified Pt compounds and DNA are thus non-covalent in nature. This embodiment is described in further detail below.

The DNA binding compounds of the present invention can be divided into three classes: 1) linear polynuclear platinum compounds, 2) branched polynuclear Pt compounds, and 3) heteronuclear compounds. The three classes are described below.

Class I. Linear Polynuclear Platinum Compounds

The general structure of the linear polynuclear platinum compounds (both covalent and non-covalent binding modes) is given below in Formula 1, where n+ represents the overall charge on the polynuclear platinum complex. X, Y, and Z are comprised of the following ligand types and any combinations thereof: am(m)ines (such as but not limited to ammonia or cyclohexylamine), aromatic planar amines (such as but not limited to pyridine, quinoline or thiazole), sulfoxides (such as but not limited to dimethylsulfoxide or methylphenylsulfoxide), and leaving groups (such as but not limited to Cl, Br, or ($C_1$–$C_4$)acyloxy).

FORMULA 1

The linear polynuclear Pt compounds may be charged and suitable counterions would be, but are not limited to, chloride (Cl$^-$) or nitrate (NO$_3^-$) in the appropriate stoichiometry (n–) for overall neutrality.

The linear polynuclear Pt compounds may be in principle subdivided into four categories, (i, ii, iii and iv) as follows:

(i) dinuclear wherein the bridging group A is formed in one of three ways. Firstly, A may be formed by diamine chains such that A=NH$_2$(CH$_2$)$_b$H$_2$N, wherein b=2–12, and is preferably 5 or 6. Or secondly, A is formed by polyamine chains such that A=NH$_2$(CH$_2$)$_b$NR(CH$_2$)$_c$H$_2$N, wherein b and c are independent and can range from 2 to 12, and are preferably 3 to 6, and R is H$_2$, (C$_1$–C$_6$ alkyl), (C$_1$–C$_6$)acyl, or (C$_1$–C$_6$) alkyloxycarbonyl. Or thirdly, A=NH$_2$(CH$_2$)$_b$NR (CH$_2$)$_c$ NR(CH$_2$)$_b$H$_2$N where b and c are independent and can range from 2 to 12, and are preferably 2 to 6, and R is H$_2$, (C$_1$–C$_6$ alkyl), (C$_1$–C$_6$acyl, or (C$_1$–C$_6$) alkyloxycarbonyl).

(ii) trinuclear containing one additional central platinum unit such that A=(NH$_2$(CH$_2$)$_b$H$_2$N)(NH$_2$(CH$_2$)$_c$H$_2$N) Pt(X)(Z) where b=2–12 and preferably 5 or 6, and c=2–12 and preferably 5 or 6, and b and c may be the same of different, and X and Z are defined as above for the general structure of the linear polynuclear platinum compounds.

(iii) tetranuclear with two central platinum units such that (A=(NH$_2$(CH$_2$)$_b$H$_2$N)Pt(X)(Z)(NH$_2$(CH$_2$)$_c$H$_2$N)Pt (X)(Z)(NH$_2$(CH$_2$)$_d$H$_2$N) and wherein b=2–12, and is preferably 5 or 6, c=2–12, and is preferably 5 or 6, d=2–12, and is preferably 5 or 6, and b, c, and d may be the same or different, and X and Z are defined as above for the general structure of the linear polynuclear platinum compounds.

(iv) pentanuclear containing three central platinum units such that (A=(NH$_2$(CH$_2$)$_b$H$_2$N)Pt(X)(Z)(NH$_2$(CH$_2$)$_c$ H$_2$N)Pt(X)(Z)(NH$_2$(CH$_2$)$_d$H$_2$N)Pt(X)(Z)(NH$_2$(CH$_2$)$_e$ H$_2$N) wherein b=12–12 and is preferably 5 or 6, c=2–12 and is preferably 5 or 6, d=2–12 and is preferably 5 or 6, e=2–12 and is preferably 5 or 6 and wherein b, c, d, and e may be the same or different, and X and Z are defined as above for the general structure of the linear polynuclear platinum compounds.

For covalent binding, the "outer units" of the binding compound always contains at least one Pt—"LG" bond where "LG" is a leaving group, preferably Cl$^-$ (i.e., at least one of the X, Y, Z ligands for each "outer unit" is a leaving group), which upon complex formation is substituted by a nucleobase of the DNA, preferably guanine. Polynuclear compounds containing only platinum are homo-(di-, tri-, tetra-, or penta-)nuclear. The structural derivatives of the binding compounds may further include compounds in which the geometry of the ligands X,Y, and Z around the platinum coordination sphere is varied with respect to cis-trans configuration. For example, the ligands Y and Z may either be mutually cis (as depicted above) or trans to each other. Further, the cis-trans configuration about different Pt coordination spheres may be the same of different within a given molecule.

Where Y=Cl and X=Z=NH$_3$, and A is a linear diamine chain of b=4 length a preferred structure becomes (1,1/t,t; n=4) as depicted in Formula 2.

FORMULA 2

Compound (1,1/t,t; n=4) has been claimed as an anti-tumor agent in U.S. Pat. No. 5,107,007 to Farrell and U.S. patent application 60/022,269 both of which, including the compounds described therein, are hereby incorporated by reference. The methods of the present invention constitute a new use for those compounds.

Where Y=Cl and X=Z=NH$_3$, and A is a polyamine chain of the type NH$_2$(CH$_2$)$_b$NR(CH$_2$)$_c$H$_2$N where b=3, c=4 and R=H$_2$ a preferred structure becomes (1,1/t,t; n=3,4) as depicted in Formula 3.

FORMULA 3

Compound (1,1/t,t; n=3,4) has been claimed as an anti-tumor agent in U.S. Pat. No. 5,107,007 to Farrell and U.S. patent application 60/022,269 both of which, including the compounds described therein, are hereby incorporated by reference. The methods of the present invention constitute a new use for those compounds.

Where Y=Cl and X=Z =NH$_3$, and A contains 1 central platinum unit of the type (NH$_2$(CH$_2$)$_b$H$_2$N)NH$_2$(CH$_2$)$_c$H$_2$N) Pt(X)(Z) where b=6 and c=6 a preferred structure becomes (1,0,1/t,t,t; n=6,6) as depicted in Formula 4.

FORMULA 4

This compound has been claimed as an anti-tumor agent in U.S. Pat. No 5,380,897 to Hoeschele et al., and U.S. Pat. No. 5,744,497 to Valsecchi, M. et al. both of which, including the compounds described therein, are hereby incorporated by reference. The methods of the present invention constitute a new use for those compounds.

Where Y=Cl and X=Z=NH$_3$, and A contains 2 central platinum units of the type (NH$_2$(CH$_2$)$_b$H$_2$N)Pt(X)(Z)(NH$_2$ (CH$_2$)$_c$H$_2$N)Pt(X)(Z)(NH$_2$(CH$_2$)$_d$H$_2$N) where b=6, c=6 and d=6, a preferred structure becomes (1,0,0,1/t,t,t,t; n=6,6,6) as depicted in Formula 5.

FORMULA 5

Where Y=Cl and X=Z=NH$_3$, and A contains 3 central platinum units of the type: (NH$_2$(CH$_2$)$_b$H$_2$N)Pt(X)(Z)(NH$_2$(CH$_2$)$_c$H$_2$N)Pt(X)(Z)(NH$_2$(CH$_2$)$_d$H$_2$N)Pt(X)(Z)(NH$_2$(CH$_2$)$_e$H$_2$N) where b=6, c=6, d=6, and e=6, a preferred structure becomes (1,0,0,0,1/t,t,t,t,t; n=6,6,6,6) as depicted in Formula 6.

the binding compounds may further include compounds in which the geometry of the ligands X, Y, and Z around the platinum coordination sphere is varied with respect to cis-trans configuration. For example, the ligands Y and Z may either be mutually cis (as depicted above) or trans to each other. Further, the cis-trans configuration about different Pt coordination spheres may be the same of different within a given molecule.

FORMULA 6

Class II. Branched Polynuclear Platinum Compounds

The above homo(di-, tri-, tetra-, or penta-)nuclear compounds contain linear diamine chains. In a further embodiment of the present invention, the compounds may also contain branched polyamine chains. Branched polyamines give rise to tri- and tetranuclear platinum compounds.

Trinuclear Compounds. The general structure of the branched trinuclear platinum compounds (both covalent and non-covalent binding modes) is given below (Formula 7) where n+ represents the overall charge on the polynuclear platinum complex. X, Y, and Z are comprised of the following ligand types and any combinations thereof. am(m)ines (such as but not limited to ammonia or cyclohexylamine), aromatic planar amines (such as but not limited to pyridine, quinoline or thiazole), sulfoxides (such as but not limited to dimethylsulfoxide or methylphenylsulfoxide), and leaving groups (such as but not limited to Cl, Br, or (C$_1$–C$_4$)acyloxy).

Where Y=Cl and X=Z=NH$_3$, and A is a polyamine chain of the type NH$_2$(CH$_2$)$_b$NR(CH$_2$)$_c$H$_2$N where b=c=2 and R=(CH$_2$)$_d$H$_2$N where d=2, a preferred structure becomes (1,1,1/t,t,t; n=2,2,2) as depicted in Formula 8:

FORMULA 8

This compound has been claimed as an anti-tumor agent in U.S. Pat. No. 5,380,897 to Hoeschele et al., which is, together with all compounds mentioned therein, hereby incorporated by reference. The methods of the present invention constitute a new use for those compounds.

FORMULA 7

The branched trinuclear compound is formed when the bridging group is a branched polyamine chain such that: A=NH$_2$(CH$_2$)$_b$NR(CH$_2$)$_c$H$_2$N where b and c are independent and can range from 2 to 12, and are preferably 2 to 6; and R is also an alkylamine chain, such that R=(CH$_2$)$_d$H$_2$N where d is from 2 to 12, and preferably 2 to 6. For covalent binding, the "outer units" of such a branched Pt compound always contains at least one Pt—"LG" bond where "LG" is a leaving group, preferably Cl⁻ (i.e., at least one of the X, Y, Z ligands for each "outer unit" is a leaving group), which upon complex formation is substituted by a nucleobase of the DNA, preferably guanine. The structural derivatives of Tetranuclear Compounds. The general structure of the branched tetranuclear platinum compounds (both covalent and non-covalent binding modes) is given below (Formula 9) where n+ represents the overall charge on the polynuclear platinum complex. X, Y, and Z are comprised of the following ligand types and any combinations thereof am(m)ines (such as but not limited to ammonia or cyclohexylamine), aromatic planar amines (such as but not limited to pyridine or thiazole), sulfoxides (such as but not limited to dimethylsulfoxide or methylphenylsulfoxide), and leaving groups (such as but not limited to Cl, Br, or (C$_1$–C$_4$)acyloxy).

FORMULA 9

The branched tetranuclear compound is formed when the bridging group is a branched polyamine chain such that $A=NH_2(CH_2)_bNR_1(CH_2)_cNR_2(CH_2)_dH_2N$ where b, c and d are independent and can range from 2 to 12, and are preferably 2 to 6, and $R_1$ is an alkylamine chain such that $R_1=(CH_2)_eH_2N$ where e is from 2 to 12, and is preferably 2 to 6, and $R_2$ is an alkylamine chain such that $R_2=(CH_2)_f H_2N$ where f is from 2 to 12, and is preferably 2 to 6. For covalent binding, the "outer units" always contains at least one Pt—"LG" bond where "LG" is a leaving group preferably Cl (i.e., at least one of the X, Y, Z ligands for each "outer unit" is a leaving group), which upon complex formation is substituted by a nucleobase of the DNA, preferably guanine. For non-covalent binding, any combination of X, Y, and Z as defined above is acceptable (i.e., the necessity of incorporating leaving groups on the "outer units" is no longer required). The structural derivatives of the binding compounds may further include compounds in which the geometry of the ligands X, Y, and Z around the platinum coordination sphere is varied with respect to cis-trans configuration. For example, the ligands Y and Z may either be mutually cis (as depicted above) or trans to each other. Further, the cis-trans configuration about different Pt coordination spheres may be the same of different within a given molecule.

Where $Y=Cl$ and $X=Z=NH_3$, and A is a polyamine chain of the type $NH_2(CH_2)_bNR_1(CH_2)_cNR_2(CH_2)_dH_2N$ where b=3, d=3 and c=4 and $R_1=(CH_2)_eH_2N$ where e=3, and $R_2=(CH_2)_fH_2N$ where f=3 (i.e. $R_1$ and $R_2$ are the same) a preferred structure becomes (1,1,1,1/t,t,t,t; n=3,3,(4),3,3) as depicted in Formula 10:

FORMULA 10

Class III. Heterotrinuclear Platinum Compounds

In linear polynuclear platinum compounds (for example, 1,0,1/t,t,t; n=6,6), a further embodiment is to incorporate different transition metals into the central unit in place of platinum. In preferred embodiments, such compounds would be heterotrinuclear. The general structure of the linear heterotrinuclear platinum compounds (both covalent and non-covalent binding modes) is given below in Formula 11, where n+ represents the overall charge on the polynuclear platinum complex. (Note that Formula 11 is the same as Formula 1.) X, Y, and Z are comprised of the following ligand types and any combinations thereof: am(m)ines (such as but not limited to ammonia or cyclohexylamine), aromatic planar amines (such as but not limited to pyridine, quinoline or thiazole), sulfoxides (such as but not limited to dimethylsulfoxide or methylphenylsulfoxide), and leaving groups (such as but not limited to Cl, Br, or $(C_1-C_4)$ acyloxy):

FORMULA 11

The heterotrinuclear compound formed by diamine chains and a different metal center is that of the type shown in Formula 12.

FORMULA 12

In this case, $A=\{(NH_2(CH_2)_bH_2N)(NH_2(CH_2)_cH_2N)M(L)_4\}^{m+}$ where m+ is the charge on the central metal unit, a is 2–12, and is preferably 5 or 6, b is 2–12, and is preferably 5 or 6, M is another metal such as but not limited to cobalt or ruthenium, L is comprised of a variety of ligand types including monodentate $NH_3$ or pyridine, or preferably bidentate chelates such as but not limited to ethylenediamine $(NH_2(CH_2)_2H_2N)$, 2,2'-bipyridine (bpy), or 1,10-phenanthroline (phen). For covalent binding, the "outer units" always contains at least one Pt—"LG" bond where "LG" is a leaving group preferably Cl⁻ (i.e., at least one of the X, Y, and Z ligands for each "outer unit " is a leaving group), which upon complexation is substituted by a nucleobase of the DNA, preferably guanine. For non-covalent binding, any combination of X, Y, and Z as defined above is acceptable (i.e., the necessity of incorporating leaving groups on the "outer units" is no longer required). The structural derivatives of the binding compounds may further include compounds in which the geometry of the ligands X, Y, and Z around the platinum coordination sphere is varied with respect to cis-trans configuration. For example, the ligands Y and Z may either be mutually cis (as depicted above) or trans to each other. Further, the cis-trans configuration about different Pt coordination spheres may be the same of different within a given molecule.

Where $Y=Cl$ and $X=Z=NH_3$, and A is of the type such that $A=(NH_2(CH_2)_bH_2N)_2M(L)_4$ where b=6, M is cobalt (III), and L is $NH_2(CH_2)_2H_2N$, a preferred structure becomes (1,0,1/t,c,t; n=6,6 {Pt,Co,Pt}) as depicted in Formula 13.

FORMULA 13

Non-Covalent Association of Polynuclear Platinum Compounds With Oligonucleotides It is accepted that covalent attachment of platinum coordination compounds to oligonucleotides occurs through hydrolysis of the Pt—Cl bond to produce Pt—$H_2O$ species, and that then the aquo ($H_2O$) ligand is rapidly displaced by a suitable nucleobase such as guanine. Non-covalent attachment may thus be achieved by use of the above structures in high saline to prevent covalent attachment. However, a preferred method is to chemically modify all of the above structures by displacement of Cl by a non-leaving group such as but not limited to $NH_3$. For non-covalent attachment, in a preferred embodiment of the present invention, the polynuclear Pt compound is 0,0,0/t,t,t; n=6,6 (Formula 14) a structural derivative of 1,0,1/t,t,t; n=6,6 (Formula 4) formed by displacement of Cl by $NH_3$:

FORMULA 14

Figure 1:
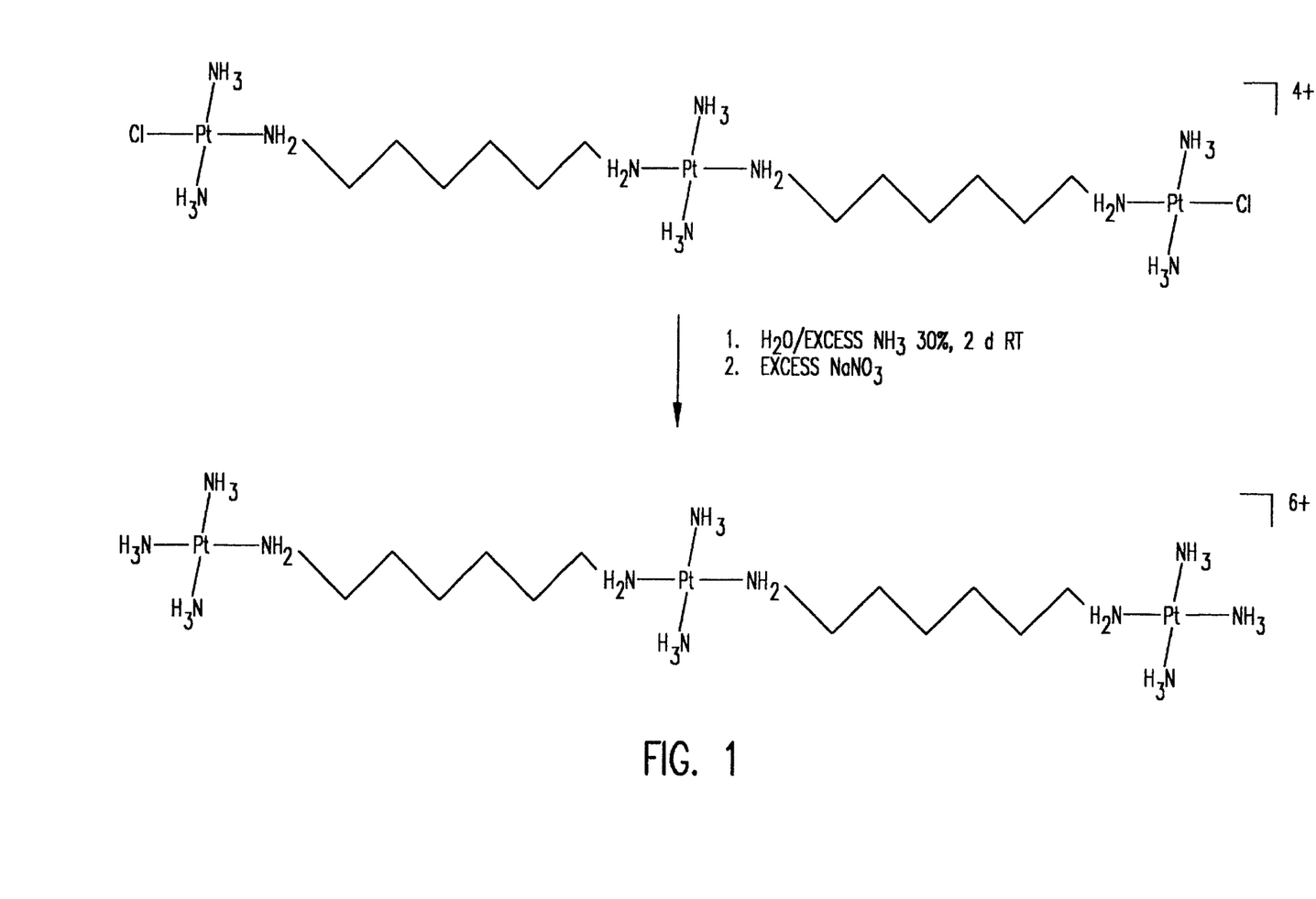
FIG. 1 shows a schematic of the conversion of 1,0,1/t,t,t n=6,6 to 0,0,0/t,t,t n=6,6.

The process of converting 1,0, 1/t,t,t; n=6,6 to 0,0,0/t,t,t; n=6,6 is illustrated in FIG. 1.

While $NH_3$ is the preferred non-leaving group, other ligands comprising of am(m)ines, mono-dentate diamines, aromatic planar amines, and sulfoxides (as described for X, Y, and Z above) can be used in similar procedures. Processes for displacing a labile leaving group such as chloride by an inert "non-leaving" group such as $NH_3$ are well known to those of skill in the art, and those of skill in the art wll recognize that such processes may be applied to any of the "covalent" binding compounds described above. The structural derivatives of the non-covalent binding compounds may further include compounds in which the geometry of the ligands X, Y, and Z around the platinum coordination sphere is varied with respect to cis-trans configuration. For example, the ligands Y and Z may either be mutually cis (as depicted above) or trams to each other. Further, the cis-trans configuration about different Pt coordination spheres may be the same of different within a given molecule.

In a preferred embodiment of the present invention, the polynuclear platinum compound is 1,0,1/t,t,t; n=6,6[trans-diammino-bis{trans-chlorodiammino$\mu$-(1,6-hexanediamino)platinum(II)}-platinum(II)tetranitrate] (Formula 4) and structural derivatives thereof. 1,0,1/t,t,t n=6,6 an anticancer agent presently in Phase I clinical trials, is the first representative of a structurally new class of platinum-based DNA-binding anti-cancer agents (Farrell and Spinelli, 1999). The drug demonstrates activity in human tumor (e.g. ovarian) xenografts resistant to cisplatin and alkylating agents, and high activity in a broad spectrum of human tumors commonly insensitive to chemotherapeutic intervention (e.g. non-small-cell lung, gastric) and characterized as p53-mutant (Perego et al., 1999). The use of 1,0,1/t,t,t n=6,6 and its structural analogs as antitumor agents are described in U.S. Pat. No. 5,744,497 to Valsecchi et al. which is a divisional of U.S. Pat. No. 5,380,897 to Hoeschele, Qu and Farrell, both of which are incorporated herein by reference.

Extensive analyses of the complexes formed between 1,0,1/t,t,t n=6,6 and single-stranded RNA, single-stranded DNA and double-stranded DNA have been carried out using gel electrophoresis and electrospray ionization Fourier transform ion cyclotron resonance mass spectrometry. These studies showed that 1,0,1/t,t,t n=6,6 preferentially binds short single-stranded DNA and short single-stranded RNA rather than double-stranded DNA.All drug development of platinum-based compounds is based on the premise that double-stranded DNA is the target and that cell death occurs as a consequence of the conformational changes brought on double-stranded DNA by the covalent attachment of the platinum atom. The significance of the finding that single-stranded DNA binds actually more rapidly to platinum compounds is that new targets and uses (with subsequent unique cellular consequences) are immediately recognised.

In a preferred embodiment of the present invention, a structural derivative of 1,0,1/t,t,t n=6,6 is utilized. The derivative is denominated 0,0,0/t,t,t n=6,6 (Formula 14). 0,0,0/t,t,t n=6,6 is capable of only non-covalent (electrostatic) interactions because the chloride leaving groups have been replaced by inert $NH_3$ groups. This analog has a 6+ charge and exhibits even higher DNA affinity than 1,0,1/t,t,t n=6,6 and is not expected to be cytotoxic since no covalent interaction with DNA is possible.

One advantage of the methods of the present invention is that ODNs with unmodified phosphodiester backbones, rather than more costly and toxic chemically modified backbones, may be used for the antisense procedures. By "unmodified" we mean that the oligodeoxynucleotides are composed of classical deoxynucleotides joined by phosphodiester linkages without further chemical modifications. However, while ODNs with unmodified phosphodiester backbones may be used, ODNs with other types of backbone chemical modifications may also be used in the practice of the present invention. For example, ODNs with phosphorothioate backbones may be used in the practice of the present invention, as may ODNs with modified sugar residues. Those of skill in the art will recognize that the DNA binding compounds of the present invention may be used to deliver any ODN, whether chemically modified or not, which exhibits a sufficiently high affinity for the binding compound to permit delivery.

Upon binding of the Pt compound to the ODN, the negative charge of the antisense ODN is neutralized, facilitating cellular uptake. Thus, another significant feature of the present invention is that no additional transfection agent is required other than the complex itself. However, an additional transfection agent may be included with the complex if desired. A variety of such transfection agents and their method of use are well-known to those of skill in the art.

While complexed to the high affinity DNA binding compounds utilized in the present invention, an ODN is protected from cellular nucleases which would otherwise degrade it. The methods of the present invention thus also provide a means of stabilizing antisense ODNs delivered to the cell.

Cellular delivery of the complexes of the present invention may be used to treat a wide variety of pathological conditions. The methods of the present invention may be used for the treatment of any condition for which the delivery of ODNs to cells may be therapeutic. For example, an antisense ODN (fomivirsen) has been approved by the FDA for the treatment of cytomegalovirus retinitis in AIDS patients. Antisense ODNs also are currently in clinical trials as single agent therapy or in combination therapy for the treatment of cancer, including non-small cell lung cancer, ovarian, breast, and pancreatic cancers (Agrawal, 1996). Those of skill in the art will recognize that any disease which is amenable to treatment by the administration of antisense ODNs may be treated by the methods of the present invention.

The selection of the particular ODN sequence to be delivered will depend on the condition which is to be treated. For example, there is currently considerable interest in discovering means of inhibiting expression of the BCL-2 protein. BCL-2 is a suppressor of apoptosis and its expression in cancer cells may contribute to the resistance of cancer cells to apoptosis. In preferred embodiments of the present invention, the antisense oligonucleotide sequences which are utilized are based on the current literature for BCL-2 regulation (Berchem, et al., 1995, Campos, et al., 1994, Webb, et al., 1997, Ziegler, et al., 1997). In a preferred embodiment of the present invention, the sequence of the ODN is d[CAGCGTGCGCCATCCTTCCC] (SEQ ID No:1). This sequence represents the most prevalent BCL-2 antisense oligodeoxynucleotide currently in cancer preclinical and clinical trials and is directed against the translational initiation (AUG) site. However, other BCL-2 related ODN sequences, or ODNs derived from genetic sequences implicated in pathological conditions other than cancer, may also be utilized in the practice of the present invention. The selection of the sequence to be utilized will depend on the condition which is to be treated. For example, the ODN sequence of d[GCCCAAGCTGGCATCCGTCA] (ISIS 2302) (SEQ ID#3) is targeted to ICAM-1 (intercellular adhesion molecules) which is involved in Crohn's disease, d[GTTCTCGCTGGTGAGTTTCA] (ISIS 3521) (SEQ ID#4) is targeted to PKC-α, and may be used as a single-agent therapy in solid tumors or in combination with standard chemotherapy, and d[UGGGGCTTACCTTGCGAACA] (GEM-132) (SEQ ID#5) which is used to treat CMV-retinitis in AIDS patients. Those of skill in the art will recognize that the present invention comprehends delivery to cells of any ODN of interest.

The compounds of the present invention may be delivered to target cells by any of several means which are well-known to those of skill in the art, and the present invention also encompasses pharmaceutical formulations which are appropriate for such delivery. For example, the complexes of the present invention may be administered intravenously as a solution. The pharmaceutical formulations of the present invention may include, in addition to the complexes of the present invention, various other ingredients such as buffers, stabilizers and the like, many examples of which are well known to those of skill in the art. The complexes of the present invention may be delivered to target cells by any method and in any form which is conducive to attaining sufficiently high (i.e. therapeutically effective) concentrations of complex within the target cells. In addition, one type of Pt compound-ODN complex may be delivered singly, or a plurality of types of Pt compound-ODN complexes may be delivered together. Both the covalent and non-covalent type complexes may be utilized. The amount of complex to be delivered to the cells will vary from patient to patient and will depend on many factors such as gender, weigh, general physical health, the condition to be treated, etc.

The present invention also provides a novel method specifically for treating cancer. The combination of antitumor active polynuclear platinum derivatives with an antisense oligodeoxynucleotide targeted to mRNA of an oncogene (for example, the BCL-2 translational initiation sequence) will potentially have a synergistic effect. In this case, the non-covalent binding structural derivatives of the compounds of the present invention will be utilized. In a preferred embodiment of this method, the non-covalent binding compound is 1,0,1/t,t,t n=6,6. The types of cancer which may be treated in this manner include but are not limited to solid tumors.

The amount of complex to be administered for the treatment of cancer will vary from patient to patient and will depend on such factors as gender, weight, age, the nature of the cancer, etc.

As a method of treatment for cancer, the non-covalent complex may be administered alone or in combination with other cancer or related therapies. For example, the complex may be administered in concert with radiation therapy, anti-nausea medication, etc. Such cancer therapy protocols are well-known to those of skill in the art. In addition, one type of Pt compound-ODN complex may be delivered singly, or a plurality of types of Pt compound-ODN complexes may be delivered together.

In addition, the complexes of the present invention may be utilized in functional genomic studies. For example, the complexes may be used in laboratory studies of cultured cells in which the delivery of ODNs to the cells serve as a means of selectively supressing gene expression.

EXAMPLES

Methods 0,0,0/t,t,t n=6,6 can be synthesized from 1,0,1/t,t,t n=6,6 and purified in a straightforward manner (see FIG. 1). Briefly, 1,0,1/t,t,t n=6,6 is treated with a 30% excess of aqueous $NH_3$ for 2 days after which time the product 0,0,0,/t,t,t, n=6,6 is precipitated with excess $NaNO_3$. Recrystallization may be effected from aqueous solution. The product is characterized by NMR spectroscopy, elementalanalysis, mass spectroscopy and purity confirmed by HPLC.

The BCL-2 oligonucleotide d[CAGCGTGCGCCATCCTTCCC] (SEQ ID #1), and the control sense oligonucleotide (also chosen based on literature references), d[GGGAAGGATGGCGCACGCTG] (SEQ ID #2) were synthesized as the unmodified phosphodiesters, and as phosphorothioate-capped oligodeoxynucleotides (the first and last linkages are phosphorothioate, the remaining linkages are phosphodiester). Oligodeoxynucleotides were gel-purified on 20% denaturing polyacrylamide gels prior to use.

End-labeling was carried out with T4 polynucleotide kinase (Life Technologies) and 5 $\mu l [\gamma$-$^{32}$P] ATP (3000 Ci/mmol) in 60 mM Tris-HCl, pH 7.8, 10 mM $MgCl_2$, 33 $\mu M$ ATP, and 15 mM 2-mercaptoethanol for 30 min at 37° C. Unincorporated nucleotide was removed by Sephadex G-25 spin columns.

The extent of complexation was monitored by gel electrophoresis. To prepare the drug:oligodeoxynucleotide complexes, increasing amounts of 1,0,1/t,t,t n=6,6 and 1,1/t,t,t n=4 (0.5:1 to 10:1 molar ratios of drug:DNA) were incubated with the 20 base $^{32}$P-end 4 labeled antisense phosphodiester oligodeoxynucleotide for 1 hour at 37° C. in H$_2$O. Reactions were terminated by ethanol precipitation. The samples were resuspended in loading buffer (80% formamide, 10 mM EDTA, pH 8, 0.025% bromophenol blue) and the complexes were electrophoresed on a 10% (19:1) denaturing polyacrylamide gel. The gel was fixed in 10% acetic acid, dried, and imaged using a Molecular Dynamics PhosphorImager and ImageQuant software.

The hybridization of d[CAGCGTGCGCCATCCTTCCC] (SEQ ID #1) complexed with 1,0,1/t,t,t n=6,6 and 1,1/t,t n=4 to BCL-2 RNA was monitored by an electrophoretic mobility shift assay. The BCL-2 RNA was in vitro transcribed from a linearized pBluescript construct which contains the human BCL-2 cDNA ORF downstream from the T7 promoter (plasmid kindly provided by Stanley Korsmeyer, Washington University) to give a 120 base transcript. The end-labeled drug:oligodeoxynucleotide complexes were prepared as described above. The complexed DNA was incubated with BCL-2 RNA in 20 mM HEPES, pH 7.3, 50 mM KCl, 10 mM MgCl$_2$, 1 mM DTT for 20 minutes at room temperature. After the incubation, loading buffer (30% glycerol in 10 mM Tris-HCl, pH 8, 1 mM EDTA, 0.025% bromophenol blue) was added and the complexes were electrophoresed on a 10% (19:1) non-denaturing polyacrylamide gel. The gel was fixed in 10% acetic acid, dried, and imaged using a Molecular Dynamics PhosphorImager and ImageQuant software.

The ability of the drug:oligodeoxynucleotide complexes hybridized to BCL-2 RNA to act as substrates for RNase H was monitored by gel electrophoresis. The drug:oligodeoxynucleotide complexes with 1,0,1/t,t,t n=6,6 and 1,1/t,t n=4 and the BCL-2 RNA were prepared as described above. The BCL-2 RNA was end-labeled as described above. The DNA-RNA complexes were hybridized in 20 mM HEPES, pH 7.3, 50 mM KCl, 10 mM MgCl$_2$, 1 mM DTT for 30 minutes at room temperature. Recombinant RNase H (Promega) was added and the reaction was incubated at 37° C. for 5 minutes. The reactions were terminated by ethanol precipitation. The pellets were resuspended in loading buffer (80% formamide, 10 mM EDTA, pH 8, 0.025% bromophenol blue) and the samples were electrophoresed on a 6% (19:1), 8.3 M urea polyacrylamide gel. The gel was fixed in 10% acetic acid, dried, and imaged using a Molecular Dynamics PhosphorImager and ImageQuant software.

Nuclease resistance of the 3:1 drug:oligodeoxynucleotide complexes was assayed in vitro using the $^{32}$P-end-labeled phosphodiester and end-capped phosphorothioate oligodeoxynucleotide, d[GGGAAGGATGGCGCACGCTG] (SEQ ID #2), complexed with 1,0,1/t,t,t n=6,6 and 1,1/t,t n=4. The complexes were prepared as described above and were incubated in RPMI 1640 supplemented with 10% fetal bovine serum (Life Technologies) at 37° C. for 48 hours. Aliquots were removed at regular timepoints and purified by phenol extraction and ethanol precipitation. The pellets were resuspended in loading buffer (80% formamide, 10 mM EDTA, pH 8, 0.025% bromophenol blue) and the samples were electrophoresed on a 20% (19:1), 8.3 M urea polyacrylamide gel at 50° C. The gel was fixed in 10% acetic acid, dried, and imaged using a Molecular Dynamics PhosphorImager and ImageQuant software. The amount of intact drug:oligodeoxynucleotide complex at each timepoint was quantitated using ImageQuant software.

EXAMPLE 1

Figure 2:
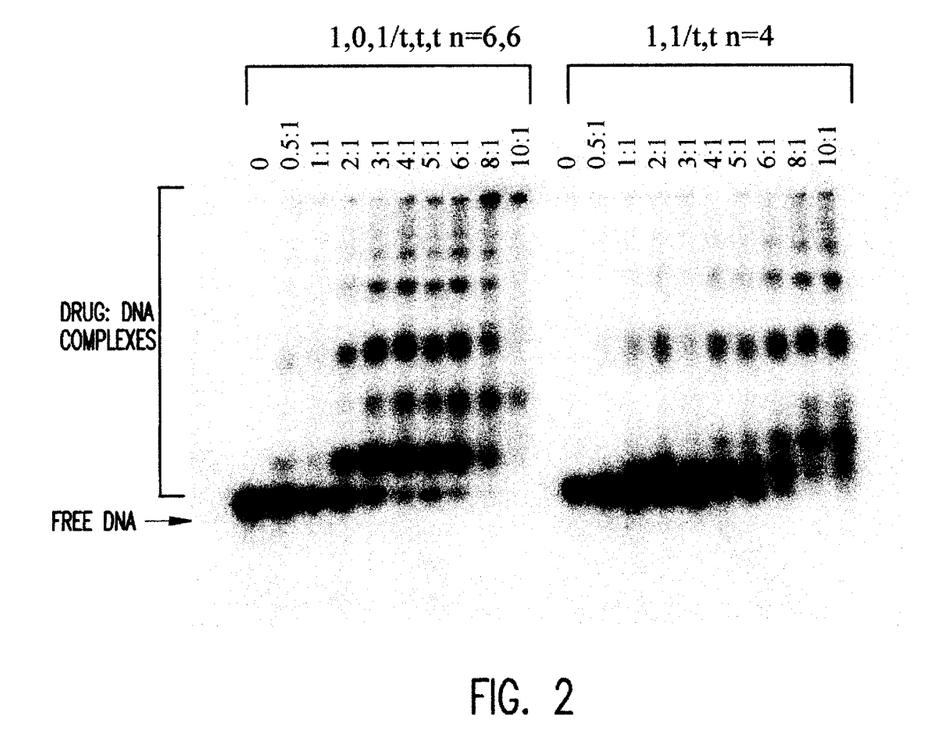
FIG. 2 is a phosphorimage of the gel of increasing molar ratios of 1,0,1/t,t,t n=6,6 and 1,1/t,t n=4 complexed to d[CAGCGTGCGCCATCCTTCCC] (SEQ ID No:1).

Complexation of High Affinity DNA Binding Molecules and Antisense Oligonucleotides The BCL-2 translational start site (AUG) related oligonucleotide d[CAGCGTGCGCCATCCTTCCC] (SEQ ID #1), was end-labeled and subsequently incubated (100 nM final concentration of oligonucleotide) with increasing amounts of 1,0,1/t,t,t n=6,6 and 1,1/t,t n=4 (0.5:1 to 10:1 final molar ratio drug:DNA). The resulting complexes were analyzed by gel electrophoresis as described in Methods and the results are shown in FIG. 2. The following was noted: multiple species were present, indicating complexation between 1,0,1/t,t,t n=6 and 1,1/t,t n=4 and the ODN. Complexation occurred at molar ratios as low as 0.5:1 drug:oligonucleotide. Thus, this high affinity DNA binding compound interacts strongly with single-stranded DNA and can adequately neutralize the phosphate backbone negative charge.

EXAMPLE 2

Hybridization of Drug:Oligo Complexes to BCL-2 RNA

Figure 3:
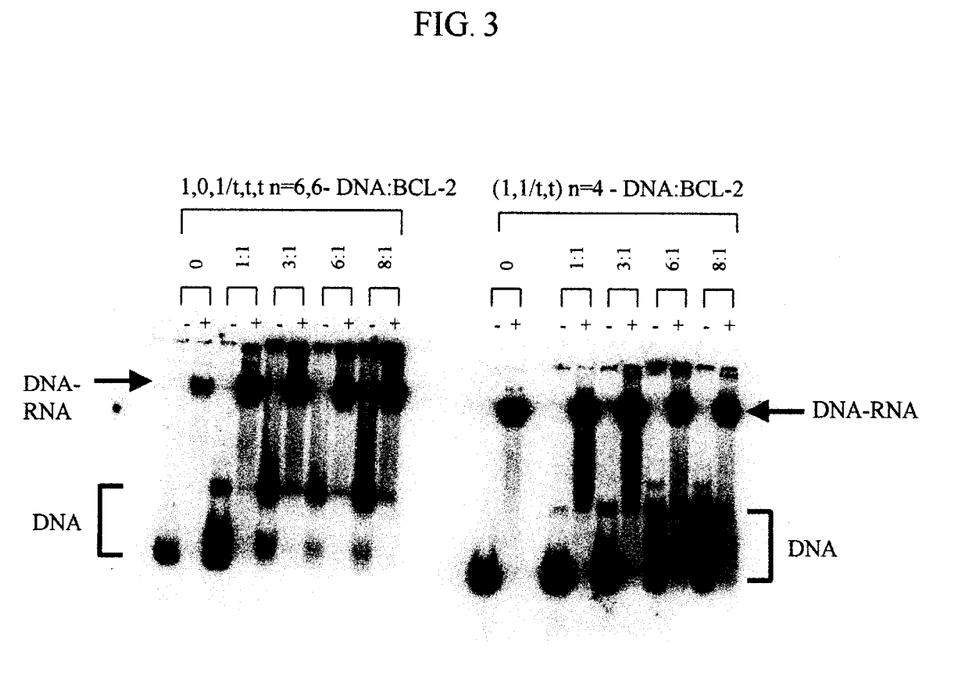
FIG. 3 is a phosphorimage of the gel showing hybridization of the drug:oligodeoxynucleotide complexes to an in vitro transcribed segment of BCL-2 RNA using 1,0,1/t,t,t n=6,6 and 1,1/t,t n=4.

The hybridization of d[CAGCGTGCGCCATCCTTCCC] (SEQ ID #1) complexed with 1,0,1/t,t,t n=6,6 and 1,1/t,t n=4 to BCL-2 RNA was monitored by an electrophoretic mobility shift assay. The resulting complexes were analyzed by gel electrophoresis as described in Methods and the results are presented in FIG. 3. The following was noted: the presence of the drug covalently attached to the antisense oligodeoxynucleotide does not interfere with the DNA-RNA hybridization reaction.

EXAMPLE 3

RNase H Assay of Drug:Oligo:BCL-2 RNA

Figure 4:
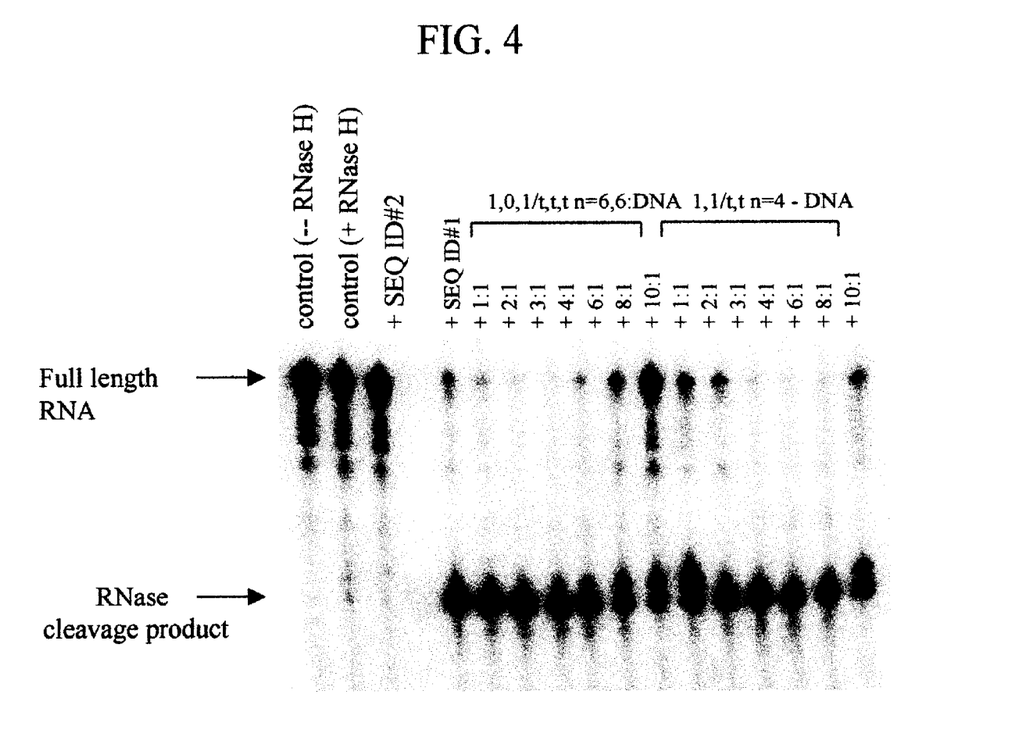
FIG. 4 is a phosphorimage of the gel illustrating that the drug:oligodeoxynucleotide complexes hybridized to BCL-2 RNA are substrates for RNase H.

The BCL-2 RNA was end-labeled and subsequently incubated with increasing molar ratios of drug:oligodeoxynucleotide complexes (1:1 to 10:1). Recombinant RNase H was added and the resulting products were analyzed by gel electrophoresis as described in Methods and the results are presented in FIG. 4. The following was noted: the drug:oligonucleotide complexes, when hybridized to BCL-2 RNA, are substrates for RNase H.

EXAMPLE 4

Nuclease Resistance of High-Affinity DNA Binders Complexed to ODNs.

Figure 5:
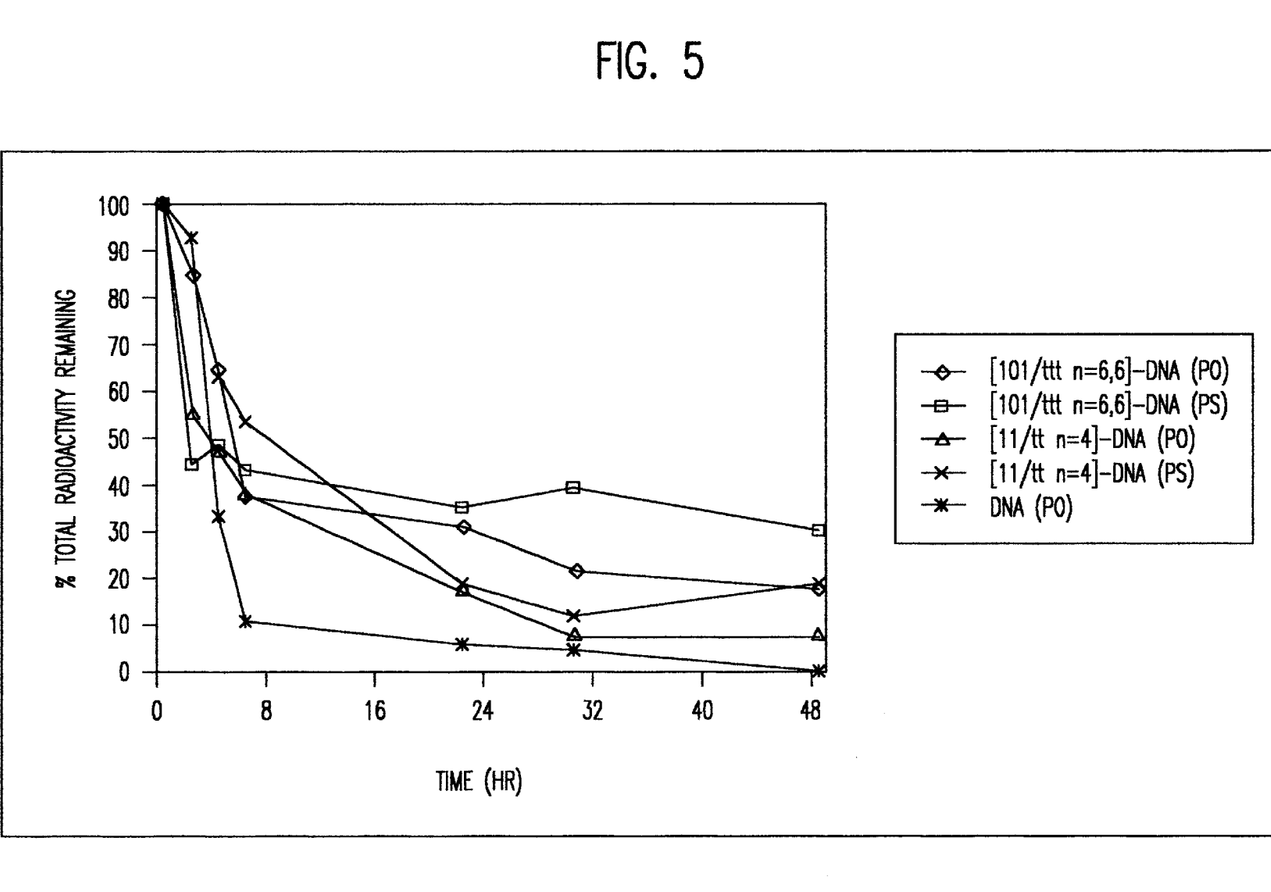
FIG. 5 is a graph showing the extent of nuclease resistance of 1,0,1/t,t,t n=6,6 and 1,1/t,t n=4 complexed to unmodified phosphodiester and phosphorothioate-capped d[GGGAAGGATGGCGCACGCTG] (SEQ ID No:2) in the presence of RPMI 1640 media supplemented with 10% fetal bovine serum.

The end-labeled phosphodiester and phosphorothioate-capped oligonucleotide, d[GGGAAGGATGGCGCACGCTG] (SEQ ID #2) (250 nM final concentration), were pre-incubated in H$_2$O with 1,0,1/t,t,t n=6,6 and 1,1/t,t n=4 at a 3:1 molar ratio as described in Methods and the results are presented in FIG. 5. The following was noted: the untreated phosphodiester oligodeoxynucleotide was significantly degraded after 6 hours, however the 1,0,1/t,t,t n=6,6 and 1,1/t,t n=4 complexed oligodeoxynucleotides showed more resistance to nuclease degradation. Thus, complexation of the ODN to the polynuclear platinum compounds protected the ODN from degradation by nucleases.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Agrawal, S. Trends *Trends Biotechnol* (1996) 14: 376–87.

Agrawal, S. and Zhang, R. *Ciba Found Symp* (1997) 209: 60–75.

Altmann, K., Fabbro, D. and Geiger, T., in *Advances in DNA Sequence-Specific Agents* M. Palumbo, Ed. (JAI Press Inc., Greenwich, Conn., 1998), vol. 3, pp. 227–266.

Arndt, G. M. and Rank, G. H. *Genome* (1997) 40: 785–97.

Benimetskaya, L., Takle, G. B., Vilenchik, M., Lebedeva, I., Miller, P. and Stein, C. A. *Nucleic Acids Res* (1998) 26: 5310–7.

Berchem, G. J., Bosseler, M., Sugars, L. Y., Voeller, H. J., Zeitlin, S. and Gelmann, E. P. *Cancer Res* (1995) 55: 735–8.

Bielinska, A., Kukowska-Latallo, J. F., Johnson, J., Tomalia, D. A. and Baker, J. R., Jr. *Nucleic Acids Res* (1996) 24: 2176–82.

Branch, A. D. *Trends Biochem Sci* (1998) 23: 45–50.

Campos, L., Sabido, O., Rouault, J. P. and Guyotat, D. *Blood* (1994) 84: 595–600.

Chaloin, L., Vidal, P., Lory, P., Mery, J., Lautredou, N., Divita, G. and Heitz, F. *Biochem Biophys Res Commun* (1998) 243: 601–8.

Cramer, H., Player, M. R. and Torrence, P. F. *Bioorg Med Chem Lett* (1999) 9: 1049–54.

Crooke, S. T. *Annu Rev Pharmacol Toxicol* (1992) 32: 329–76.

Crooke, S. T. *Ciba Found Symp* (1997) 209: 158–164.

Crooke, S. T. *Biotechnol Genet Eng Rev* (1998) 15: 121–57.

Denizot, F. and Lang, R. *J Immunol Methods* (1986) 89: 271–7.

Farrell, N. *Cancer Invest.* (1993) 11: 578–589.

Farrell, N. *Met. Ions Biol Syst.* (1996) 32: 603–639.

Farrell, N. and Spinelli, S. (1999) in *Uses of inorganic Chemistry in Medicine* (Farrell, N., Ed.)

Flanagan, W. M., Wagner, R. W., Grant, D., Lin, K. Y. and Matteucci, M. D.*Nat Biotechnol* (1999) 17: 48–52.

Flanagan, W. M., Wolf, J. J., Olson, P., Grant, D., Lin, K. Y., Wagner, R. W. and Matteucci, M. D. *Proc Natl Acad Sci USA* (1999) 96:3513–8.

Gokhale, P. C., Soldatenkov, V., Wang, F. H., Rahman, A., Dritschilo, A. and Kasid, U. *Gene Ther* (1997) 4: 1289–99.

Good, L. and Nielsen, P. E. *Antisense Nucleic Acid Drug Dev* (1997) 7: 431–7.

Guerrier-Takada, C., Li, Y. and Altman, S. *Proc Natl Acad Sci USA* (1995) 92: 11115–9.

Helin, V., Gottikh, M., Mishal, Z., Subra, F., Malvy, C. and Lavignon, M. *Biochem Pharmacol* (1999) 58: 95–107.

Hope, M. J., Mui, B., Ansell, S. and Ahkong, Q. F. *Mol Membr Biol* (1998) 15: 1–14.

Inouye, M., Mao, J. R., Shimamoto, T. and Inouye, S. *Ciba Found Symp* (1997) 209: 224–233.

Janout, V., Lanier, M., Deng, G. and Regen, S. L. *Bioconjug Chem* (1997) 8: 891–5.

Juliano, R. L., Alahari, S., Yoo, H., Kole, R. and Cho, M. *Pharm Res* (1999) 16: 494–502.

Kloster, M. B. G., Hannis, J. C., Muddiman, D. C. and Farrell, N. (1999) submitted.

Kohler, U., Ayre, B. G., Goodman, H. M. and Haseloff, J. *J Mol Biol* (1999) 285: 1935–50.

Lavrovsky, Y., Chen, S. and Roy, A. K. *Biochem Mol Med* (1997) 62: 11–22.

Ma, M. Y., Jacob-Samuel, B., Dignam, J. C., Pace, U., Goldberg, A. R. and George, S. T. *Antisense Nucleic Acid Drug Dev* (1998) 8: 415–26.

McKay, R. A., Cummins, L. L., Graham, M. J., Lesnik, E. A., Owens, S. R., Winniman, M. and Dean, N. M. *Nucleic Acids Res* (1996) 24: 411–7.

Monia, B. P. *Ciba Found Symp* (1997) 209: 107–119.

Monia, B. P., Lesnik, E. A., Gonzalez, C., Lima, W. F., McGee, D., Guinosso, C. J., Kawasaki, A. M., Cook, P. D. and Freier, S. M. *J Biol Chem* (1993) 268: 14514–22.

Murakami, A., Yoshimoto, A., Furumoto, A., Namba, M. and Yamaoka, T. *Nucleic Acids Symp Ser* (1995) 229–30.

Nielsen, P. E. *Curr Opin Struct Biol* (1999) 9: 353–7.

Perego, P., Caserini, C., Gatti, L., Carenini, N., Romanelli, S., Supino, R., Colangelo, D., Viano, I., Leone, R., Spinelli, S., Pezzoni, G., Manzotti, C., Farrell, N., and Zunino, F. *Mol Pharmacol* (1999) 55: 528–34.

Rossi, J. J. *Ciba Found Symp* (1997) 209: 195–204.

Rump, E. T., de Vrueh, R. L., Sliedregt, L. A., Biessen, E. A., van Berkel, T. J. and Bijsterbosch, M. K. *Bioconjug Chem* (1998) 9: 341–9.

Spiller, D. G., Giles, R. V., Grzybowski, J., Tidd, D. M. and Clark, R. E. *Blood* (1998) 91: 4738–46.

Summerton, J. and Weller, D. *Antisense Nucleic Acid Drug Dev* (1997) 7: 187–95.

Talkle, G. B., Thierry, A. R., Flynn, S. M., Peng, B., White, L., Devonish, W., Galbraith, R. A., Goldberg, A. R. and George, S. T. *Antisense Nucleic Acid Drug Dev* (1997) 7: 177–85.

Thierry, A. R. and Dritschilo, A. *Nucleic Acids Res* (1992) 20: 5691–8.

Verheijen, J. C., van der Marel, G. A., van Boom, J. H., Bayly, S. F., Player, M. R. and Torrence, P. F. *Bioorg Med Chem* (1999) 7: 449–55.

Webb, A., Cunningham, D., Cotter, F., Clarke, P. A., di Stefano, F., Ross, P., Corbo, M. and Dziewanowska, Z. *Lancet* (1997) 349: 1137–41.

Weiss, B., Davidkova, G. and Zhou, L. W. *Cell Mol Life Sci* (1999) 55: 334–58.

Wu, P. K., Kharatishvili, M., Qu, Y., Farrell, N., *J Inorg Biochem* (1996) 63: 9–18.

Xiao, W., Li, G., Player, M. R., Maitra, R. K., Waller, C. F., Silverman, R. H. and Torrence, P. F. *J Med Chem* (1998) 41: 1531–9.

Yonish-Rouach, E. *Experientia* (1996) 52: 1001–7.

Ziegler, A., Luedke, G. H., Fabbro, D., Altmann, K. H., Stahel, R. A. and Zangemeister-Wittke, U. *J Natl Cancer Inst* (1997) 89: 1027–36.

We claim:

1. A method for the delivery of an antisense oligodeoxynucleotide to cells, comprising the steps of, forming a complex comprising said oligodeoxynucleotide and a polynuclear platinum compound, and providing said complex to cells.

2. The method of claim 1 wherein said polynuclear platinum compound has the structural formula:

wherein X, Y and Z are selected from the group consisting of: am(m)ines, mono-dentate diamines, aromatic planar amines, sulfoxides and leaving groups;

A is selected from the group consisting of:

$NH_2(CH_2)_bH_2N$, wherein b=2–12;

$NH_2(CH_2)_bNR(CH_2)_cH_2N$, wherein b and c range from 2 to 12, and R is selected from the group consisting of: $H_2$, $(C_1-C_6$ alkyl), $(C_1-C_6)$acyl, and $(C_1-C_6)$ alkyloxycarbonyl;

$NH_2(CH_2)_bNR(CH_2)_cNR(CH_2)_dH_2N$ wherein b, c and d range from 2 to 12, and R is selected from the group consisting of: $H_2$, $(C_1-C_6$ alkyl), $(C_1-C_6)$acyl, and $(C_1-C_6)$alkyloxycarbonyl);

$(NH_2(CH_2)_bH_2N)(NH_2(CH_2)_cH_2N)Pt(X)(Z)$ wherein b and c range from 2–12, and X and Z are selected from the group consisting of: am(m)ines, mono-dentate diamines, aromatic planar amines, sulfoxides and leaving groups;

$(NH_2(CH_2)_bH_2N)Pt(X)(Z)(NH_2(CH_2)_cH_2N)Pt(X)(Z)$ $(NH_2(CH_2)_dH_2N)$ and wherein b, c and d range from 2–12, and X and Z are selected from the group consisting of: am(m)ines, mono-dentate diamines, aromatic planar amines, sulfoxides and leaving groups;

$(NH_2(CH_2)_bH_2N)Pt(X)(Z)(NH_2(CH_2)_cH_2N)Pt(X)(Z)$ $(NH_2(CH_2)_dH_2N)Pt(X)(Z)(NH_2(CH_2)_eH_2N)$ wherein b, c, d, and e range from 2–12 and X and Z are selected from the group consisting of: am(m)ines, mono-dentate diamines, aromatic planar amines, sulfoxides and leaving groups;

$\{(NH_2(CH_2)_aH_2N)(NH_2(CH_2)_bH_2N)M(L)_4\}^{m+}$ wherein a and b range from 2–12, M is a non-platinum metal, L is a ligand selected from the group consisting of: monodentate and bidentate chelates, and m+ is the charge on the non-platinum metal, and n+ is the charge on said polynuclear platinum compound.

3. The method of claim 1 wherein said polynuclear platinum compound has the structural formula:

wherein $A=NH_2(CH_2)_bNR(CH_2)_cH_2N$ where $R=(CH_2)_dH_2N$ and b, c and d range from 2 to 12;

X, Y and Z are selected from the group consisting of: am(m)ines, mono-dentate diamines, aromatic planar amines, sulfoxides and leaving groups; and n+ represents the overall charge on said polynuclear platinum compound.

4. The method of claim 1 wherein said polynuclear platinum compound has the structural formula:

wherein $A=NH_2(CH_2)_bNR_1(CH_2)_cNR_2(CH_2)_dH_2N$, where $R_1=(CH_2)_eH_2N$, $R_2=(CH_2)_fH_2N$ and b, c, d, e and f range from 2 to 12;

X, Y and Z are selected from the group consisting of: am(m)ines, mono-dentate diamines, aromatic planar amines, sulfoxides and leaving groups; and n+ represents the overall charge on said polynuclear platinum compound.

5. The method of claim 1 wherein said oligodeoxynucleotide is an unmodified phosphodiester oligodeoxynucleotide.

6. The method of claim 1 wherein said polynuclear platinum compound is 1,0,1/t,t,t n=6,6.

7. The method of claim 1 wherein said polynuclear platinum compound is a structural derivative of 1,0,1/t,t,t n=6,6.

8. The method of claim 7 wherein said structural derivative of 1,0,1/t,t,t n=6,6 is 0,0,0/t,t,t n=6,6.

9. A method for the treatment of cancer in a patient in need thereof, comprising the steps of:

forming a complex comprising an oligodeoxynucleotide and a polynuclear platinum compound, wherein said polynuclear platinum compound is selected from the group consisting of 1,0,1/t,t,t n=6,6 and a structural derivative of 1,0,1/t,t,t n=6,6 and administering said complex to said patient.

10. The method of claim 9 wherein said polynuclear platinum compound is 1,0,1/t,t,t n=6,6.

11. The method of claim 9 wherein said polynuclear platinum compound is a structural derivative of 1,0,1/t,t,t n=6,6.

12. The method of claim 11 wherein said structural derivative of 1,0,1/t,t,t n=6,6 is 0,0,0/t,t,t n=6,6.

13. The method of claim 9 wherein the sequence of said oligodeoxynucleotide is SEQ ID NO: 1.

14. A composition comprising a single-stranded oligodeoxynucleotide, and a polynuclear platinum compound complexed with said single-stranded oligodeoxynucleotide wherein said polynuclear platinum compound is selected on the group consisting of i) a polynuclear platinum compound having the structural formula:

wherein X, Y and Z are selected from the group consisting of: am(m)ines, mono-dentate diamines, aromatic planar amines, sulfoxides and leaving groups;

A is selected from the group consisting of:

$NH_2(CH_2)_b H_2N$, wherein b=2–12

$NH_2(CH_2)_b NR(CH_2)_c H_2N$, wherein b and c range from 2 to 12, and R is selected from the group consisting of: $H_2$, ($C_1$–$C_6$ alkyl), ($C_1$–$C_6$)acyl, and ($C_1$–$C_6$) alkyloxycarbonyl;

$NH_2(CH_2)_b NR(CH_2)_c NR(CH_2)_d H_2N$ wherein b, c and d range from 2 to 12, and R is selected from the group consisting of: $H_2$, ($C_1$–$C_6$ alkyl), ($C_1$–$C_6$)acyl, and ($C_1$–$C_6$)alkyloxycarbonyl);

$(NH_2(CH_2)_b H_2N)(NH_2(CH_2)_c H_2N)Pt(X)(Z)$ wherein b and c range from 2–12, and X and Z are selected from the group consisting of: am(m)ines, mono-dentate diamines, aromatic planar amines, sulfoxides and leaving groups;

$(NH_2(CH_2)_b H_2N)Pt(X)(Z)(NH_2(CH_2)_c H_2N)Pt(X)(Z)$ $(NH_2(CH_2)_d H_2N)$ and wherein b, c and d range from 2–12, and X and Z are selected from the group consisting of: am(m)ines, mono-dentate diamines, aromatic planar amines, sulfoxides and leaving groups;

$(NH_2(CH_2)_b H_2N)Pt(X)(Z)(NH_2(CH_2)_c H_2N)Pt(X)(Z)$ $(NH_2(CH_2)_d H_2N)Pt(X)(Z)(NH_2(CH_2)_e H_2N)$ wherein b, c, d, and e range from 2–12 and X and Z are selected from the group consisting of: am(m)ines, mono-dentate diamines, aromatic planar amines, and sulfoxides;

$\{(NH_2(CH_2)_a H_2N)(NH_2(CH_2)_b H_2N)M(L)_4\}^{m+}$ wherein a and b range from 2–12, M is a non-platinum metal, L is a ligand selected from the group consisting of: monodentate and bidentate chelates, and m+ is a charge on the non-platinum metal, and n+ is a charge on said polynuclear platinum compound;

ii) a polynuclear platinum compound having the structural formula:

wherein $A=NH_2(CH_2)_b NR(CH_2)_c H_7 N$ where $R=(CH_2)_d H_2 N$ and b, c and d range from 2 to 12;

X, Y and Z are selected from the group consisting of; am(m)ines, mono-dentate diamines, aromatic planar amines, sulfoxides and leaving groups; and n+ represents an overall charge on said polynuclear platinum compound; and iii) a polynuclear platinum compound having the structural formula:

wherein $A=NH_2(CH_2)_b NR_1(CH_2)_c NR_c(CH_2)_d H_2N$, where $R_1=(CH_2)_e H_2N$, $R_2=(CH_2)_f H_2N$ and b, c, d, e and f range from 2 to and 12;

X, Y and Z are selected from the group consisting of: am(m)ines, mono-dentate diamines, aromatic planar amines, sulfoxides and leaving groups; and n+ represents an overall charge on said polynuclear platinum compound.

15. The composition of claim 14 wherein said polynuclear platinum compound is complexed with said single-stranded oligodeoxynucleotide by covalent bonds.

16. The composition of claim 14 wherein said polynuclear platinum compound is complexed with said single-stranded oligodeoxynucleotide by electrostatic bonds.

17. The composition of claim 14 wherein said polynuclear platinum compound is selected from the group consisting of: 1,0,1/t,t,t n=6,6 and 0,0,0/t,t,t n=6,6.

18. A polynuclear platinum compound having the structural formula:

wherein X, Y and Z are selected from the group consisting of: am(m)ines, mono-dentate diamines, aromatic planar amines, sulfoxides and leaving groups;

A is selected from the group consisting of:

$NH_2(CH_2)_b NR(CH_2)_c H_2N$, wherein b and c range from 2 to 12, and R is selected from the group consisting of: $H_2$, ($C_1$–$C_6$ alkyl), ($C_1$–$C_6$)acyl, and ($C_1$–$C_6$) alkyloxycarbonyl;

$NH_2(CH_2)_bNR(CH_2)_cNR(CH_2)_dH_2N$ wherein b, c and d range from 2 to 12, and R is selected from the group consisting of: $H_2$, ($C_1$–$C_6$ alkyl), ($C_1$–$C_6$)acyl, and ($C_1$–$C_6$)alkyloxycarbonyl);

$(NH_2(CH_2)_bH_2N)(NH_2(CH_2)_cH_2N)Pt(X)(Z)$ wherein b and c range from 2–12, and X and Z are selected from the group consisting of: am(m)ines, monodentate diamines, aromatic planar amines, sulfoxides;

$(NH_2(CH_2)_bH_2N)Pt(X)(Z)(NH_2(CH_2)_cH_2N)Pt(X)(Z)(NH_2(CH_2)_dH_2N)$ and wherein b, c and d are sulfoxides;

$(NH_2(CH_2)_bH_2N)Pt(X)(Z)(NH_2(CH_2)_cH_2N)Pt(X)(Z)(NH_2(CH_2)_dH_2N)$ $Pt(X)(Z)(NH_2(CH_2)_eH_2N)$ wherein b, c, d, and e range from 2–12 and X and Z are sulfoxides;

$\{(NH_2(CH_2)_aH_2N)(NH_2(CH_2)_bH_2N)M(L)_4\}^{m+}$ wherein a and b range from 2–12, M is a non-platinum metal, L is a ligand selected from the group consisting of: monodentate and bidentate chelates, and m+ is the charge on the non-platinum metal, and n+ is the charge on said polynuclear platinum compound.

19. A polynuclear platinum compound having the structural formula:

wherein $A=NH_2(CH_2)_bNR(CH_2)_cH_2N$ where $R=(CH_2)_dH_2N$ and b, c and d range from 2 to 12;

X, Y and Z are selected from the group consisting of: am(m)ines, mono-dentate diamines, aromatic planar amines, sulfoxides; and n+ represents the overall charge on said polynuclear platinum compound.

20. A polynuclear platinum compound having the structural formula wherein $A=NH_2(CH_2)_bNR_1(CH_2)_cNR_2(CH_2)_dH_2N$, where $R_1=(CH_2)_eH_2N$, $R_2=(CH_2)_fH_2N$ and b, c, d, e and f range from 2 to 12;

X, Y and Z are selected from the group consisting of: am(m)ines, monodentate diamines, aromatic planar amines, sulfoxides and leaving groups; and n+ represents an overall charge on said polynuclear platinum compound.

* * * * *